(12) United States Patent
Barlov et al.

(10) Patent No.: US 8,406,900 B2
(45) Date of Patent: Mar. 26, 2013

(54) IMPLANTABLE LEAD

(75) Inventors: Armin Barlov, Järfälla (SE); Magnus Grönvik, Kungsängen (SE)

(73) Assignee: St. Jude Medical AB, Jarfalla (SE)

( * ) Notice: Subject to any disclaimer, the term of this patent is extended or adjusted under 35 U.S.C. 154(b) by 1421 days.

(21) Appl. No.: 11/603,583

(22) Filed: Nov. 22, 2006

(65) Prior Publication Data

US 2007/0123967 A1   May 31, 2007

Related U.S. Application Data

(63) Continuation-in-part of application No. PCT/SE2005/001794, filed on Nov. 29, 2005.

(51) Int. Cl.
*A61N 1/05* (2006.01)
(52) U.S. Cl. .................................................. 607/127
(58) Field of Classification Search ............... 607/127
See application file for complete search history.

(56) References Cited

U.S. PATENT DOCUMENTS

| 5,324,325 | A | * | 6/1994 | Moaddeb | 607/120 |
| 5,447,534 | A | * | 9/1995 | Jammet | 607/127 |
| 5,658,327 | A | * | 8/1997 | Altman et al. | 607/127 |
| 6,129,751 | A | * | 10/2000 | Lucchesi et al. | 607/127 |
| 6,819,959 | B1 | * | 11/2004 | Doan et al. | 607/127 |

* cited by examiner

*Primary Examiner* — George Evanisko

(57) ABSTRACT

This invention relates to an implantable lead, which comprises a conductor; an electrode assembly, arranged at a distal end of the lead, and comprising a housing defining an internal cavity; a helical guide spring arranged in a proximal portion of the cavity and having several spaced turns, and a fixation assembly, which is rotatable relative to the housing, and which includes a shaft extending into the cavity from a proximal end of the housing; and an extendable helical fixation element attached to the shaft at a distal end thereof and protruding beyond the distal end thereof. The fixation assembly has an interaction portion, which interacts with the helical guide spring for causing longitudinal movement of the fixation element when the shaft is rotated.

16 Claims, 2 Drawing Sheets

IMPLANTABLE LEAD

RELATED APPLICATION

This application is a continuation-in-part of International Application PCT/SE2005/001794 filed on Nov. 29, 2005.

BACKGROUND OF THE INVENTION

1. Field of the Invention

The present invention relates to an implantable lead, such as for example a pacemaker lead.

2. Description of the Prior Art

In order to make sure that a lead stays in place, for example endocardially, it is provided with a helical fixation element, which is arranged at the distal end of the lead. The fixation element can be screwed into the body tissue.

One prior art example of such a lead is disclosed in U.S. Pat. No. 4,972,848. The lead has an insulative body and a conductor extending within the insulative lead body. An electrode assembly is mounted at the distal end cavity. The conductor extends into the cavity from a proximal end thereof. A helical fixation element is electrically and mechanically attached the distal end of the conductor and is extendable out of the cavity by rotating it by means of rotating the conductor. In order for the fixation element to move forward when it is being rotated it rotates around a fixed electrode guide, which is attached to the inner walls of the cavity. The radial portions connecting the centre portion with a surrounding cylindrical portion, which is fixed to the inner wall of the cavity. The turns of the fixing element extends around the centre portion and abut on the radial portions, which advance the fixation element when it is being rotated.

SUMMARY OF THE INVENTION

It is an object of the present invention to provide an implantable lead, which has a fixation element that is easily extended and retracted by rotational movement thereof.

This object is achieved, in accordance with an aspect of the present invention, by an implantable lead, which has a proximal end and a distal end, and which comprises:

a conductor having a proximal end and a distal end; an electrode assembly, arranged at the distal end of the lead, and comprising a housing defining an internal cavity and having a proximal end and a distal end, a helical guide spring arranged in a proximal portion of the cavity and having several spaced turns, and a fixation assembly, which is rotatable relative to the housing, and which comprises a shaft extending into the cavity from the proximal end of the housing, and an extendable helical fixation element attached to the shaft at the distal end thereof and protruding beyond the distal end thereof. An interaction portion of the fixation assembly interacts with the helical guide spring for causing longitudinal movement of the fixation assembly when the shaft is rotated.

In an embodiment of the lead according to the invention the interaction portion comprises a portion of the shaft having a protrusion, which extends into a space between two turns of the helical guide spring.

Due to the shaft having at least one protrusion, which slides on the turns of the guide spring, a functionally reliable and low friction solution is obtained.

In an embodiment of the lead according to the invention, the interaction portion comprises a portion of the helical fixation element having turns equally spaced as the turns of the guide spring extending in the spaces between the turns of the guide spring. Thus, in a longitudinal direction, the turns of the guide spring alternate with the terms of the helical fixation element.

In an embodiment of the lead according to the invention, the electrode assembly further comprises a first bearing for the shaft, wherein the first bearing is attached to the inner wall of the cavity, and wherein the first bearing supports the shaft between the distal end of the shaft and at the protrusion.

In this embodiment the shaft is well supported, which ensures a straight and well controlled extension movement of the fixation element.

In an embodiment of the lead according to the invention, the first and second bearings define a chamber of the cavity, which chamber is fillable with a lubricant. The lubricant filled chamber protects the feeding mechanism, i.e. the shaft rotating in the guide spring, from external fluids and particles that could impair the function.

In an embodiment of the lead according to the invention, protrusion abutment surfaces of the protrusion are shaped for minimizing the contact area between the protrusion and the turns of the guide spring. For example, the protrusion or protrusions can be post shaped, and, additionally, the cross-section of the post(s) can be circular. Thereby two curved surfaces would abut on each other, providing a very small contact area.

In an embodiment of the lead according to the invention, the shaft is connected with the conductor such that shaft co-rotates with the conductor. This embodiment is adapted to the common praxis for fastening the lead that a user is acquainted with.

In an embodiment of the lead according to the invention, the shaft is provided with several protrusions, which are symmetrically arranged around the shaft. To have more than one protrusion will further stabilize the screw operation and distribute the applied force evenly in relation to the central axis of the shaft, that is the sum of the torques generated by the force exerted on the protrusions, about a transverse axis, becomes close to zero.

These and other aspects, features, and advantages of the invention will be apparent from and elucidated with reference to the embodiments described hereinafter.

DESCRIPTION OF THE PREFERRED EMBODIMENTS

Figure 1:
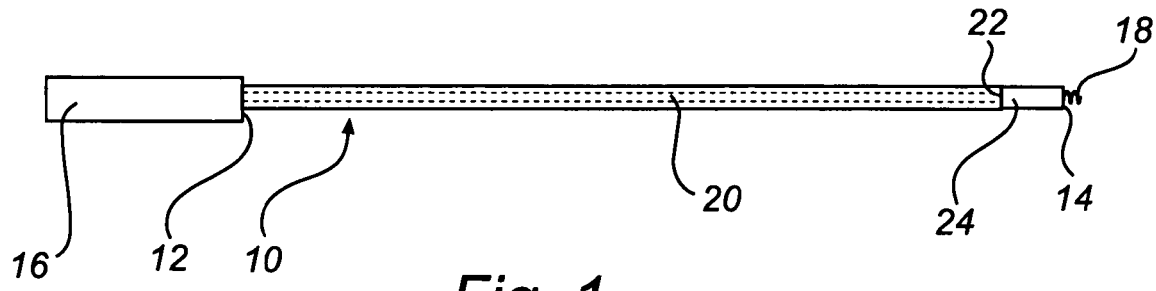
FIG. 1 is a side view of a lead.

Referring to FIG. 1 an implantable lead 10 has a proximal end 12 and a distal end 14. At the proximal end 12 thereof the lead 10 is provided with an operating device 16 for fastening the lead in body tissue by a screwing operation, wherein a helical fixation element 18 is extended out of the distal end 14 of the lead 10. The lead 10 further comprises a rotatable conductor 20 having a proximal end substantially coinciding with the proximal end 12 of the lead 10 and a distal end 22 close to the distal end 14 of the lead 10. The lead 10 further comprises an electrode assembly 24, which is arranged at the distal end 14 of the lead 10.

Figure 2:
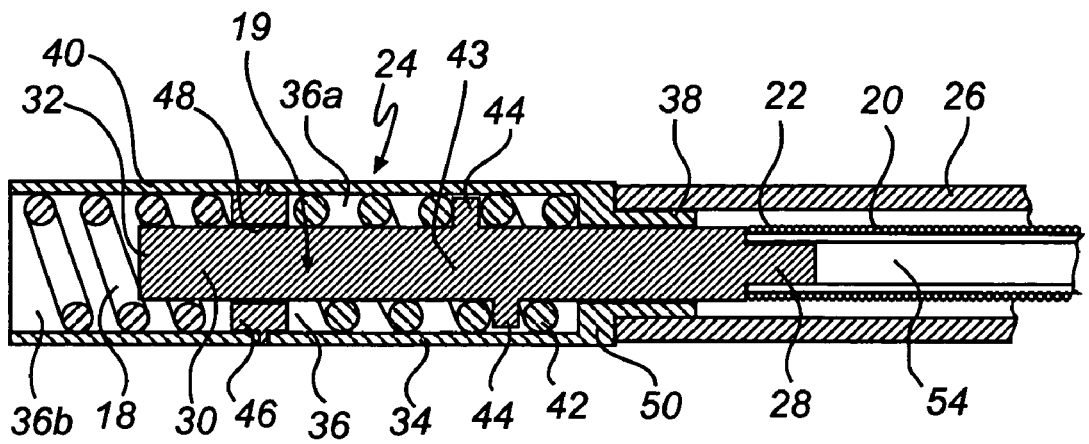
FIGS. 2 and 3 are sectional views along a distal end portion of an embodiment of a lead according to the present invention.
Figure 3:
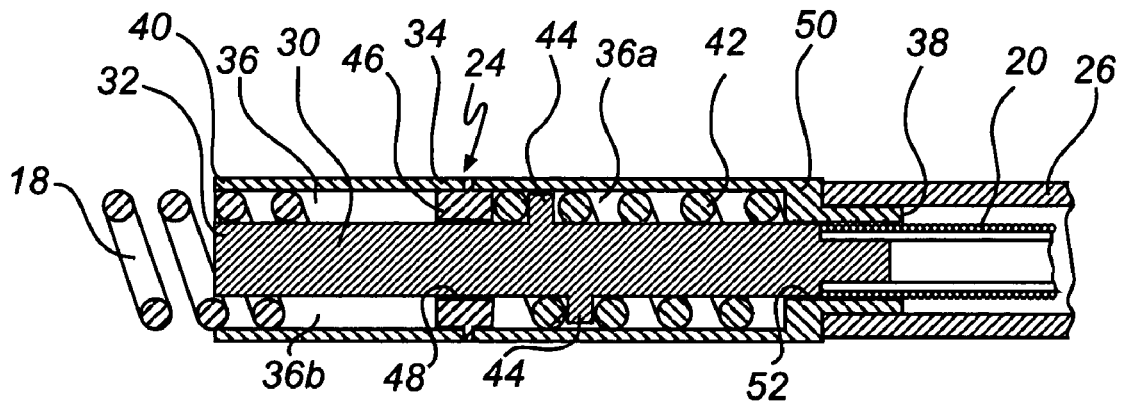

An enlarged view of a distal end portion of the lead 10, including the electrode assembly 24, is schematically shown in FIGS. 1 and 2. The lead 10 further comprises an elongated insulating tube 26 arranged coaxially of the conductor 20. Thus, the conductor 20 extends within an inner cavity of the tube 26. The distal end 22 of the conductor is attached to a proximal end 28 of a shaft 30, which is comprised in the electrode assembly. More particularly, the conductor 20 comprises coil, which is fixed, for example, welded, on the proximal end 28 of the shaft 30, thereby having mechanical as well as electrical contact with the shaft 30. The fixation element 18 and the shaft 30 are parts of a fixation assembly 19. The fixation element 18 is attached, for example welded, to the distal end 32 of the shaft 30. In FIG. 2 the fixation element 18 is shown in a retracted position, and in FIG. 3 it is shown in an extended position. When extended it is in engagement with body tissue, thereby fixing the lead in place while acting as an electrode for transmitting electrical signals to the body. For example the lead 10 is a pacemaker lead providing pacing stimuli to the heart.

The electrode assembly 24 comprises a housing 34, which defines an internal longitudinal cavity 36 and which has a proximal end 38 and a distal end 40. The insulating tube 26 is attached to the proximal end 38 of the housing 34. The shaft 30 extends into the cavity 36 from the proximal end 38 of the housing 34. The fixation assembly 19 is rotatable, i.e. the shaft 30 and the fixation element 18 are rotatable, relative to the housing 34.

The electrode assembly 24 further comprises a helical guide spring 42, which is arranged in a proximal portion 36a of the cavity 36. The guide spring 42 has several turns, in the figures about 4 turns, which are spaced from each other. The fixation assembly 19 has an interaction portion 43, which interacts with the guide spring 42 for causing longitudinal movement of the fixation assembly 19 when the shaft 30 is being rotated. In this embodiment the interaction portion 43 is a portion of the shaft having protrusions 44, which are received in spaces between the turns of the guide spring 42. In this embodiment, the protrusions are two posts, in the form of cylindrical pins, 44, which are arranged on diametrically opposite sides of the shaft and longitudinally displaced relative to each other. Thus, each post 44 extend into the space between two adjacent turns of the guide spring 42. An alternative embodiment having a single post would work, but two or more posts, which are strategically located over the surface of the shaft 30, are preferable. When the shaft 30 is rotated the posts 44 slides on the surfaces of the turns. Preferably the contact area between the posts 44 and the guide spring 42 is minimized. In the illustrated embodiment the cross-section of the guide spring turns is circular, and so is the cross-section of the posts 44. Thus spring abutment surfaces of the posts 44 and corresponding post abutment surfaces of the turns, which abut on each other, are curved. However, various shapes of abutment surfaces and cross-sections are possible in principle, such as for example a square or semicircular cross-section, and flat abutment surfaces or some other shape of the abutment surfaces.

In this embodiment, the guide spring and the fixation element have the same pitch, and also diameter. It is possible to manufacture them from the same helical spring work-piece.

The electrode assembly 24 further comprises a first, or distal, bearing 46, which is arranged about in the middle between the proximal end 38 and the distal end 40 of the housing 34, thereby partitioning the cavity 36 in the proximal and distal portions 36a, 36b. The first bearing 46 is attached to the inner wall of the housing 34, and it has a through boring 48 through which the shaft 30 extends. Thus, the ring shaped surface of the boring 48 acts as a supporting seat for the shaft 30. A second bearing 50 is formed at the proximal end 38 of the housing 34, and it has a through boring 52 supporting the shaft 30. The bearings 46, 50 define a chamber, constituting the proximal portion 36a of the cavity 36. The chamber 36a is filled with a lubricant for ensuring and facilitating the rotatability of the shaft 30. Consequently, the posts 44 of the shaft 30 and the guide spring 42 are located in the chamber 36a.

When the lead has been introduced into the body, for example through veins, and the distal end of the lead 10 has arrived at the aimed at position, such as in the coronary sinus, the fixation element is still withdrawn as in FIG. 2. Then the conductor 20 is rotated by means of the operating device 16, which moves the shaft 30 ahead towards the distal end of the housing 34, and which moves the fixation element 18 out of the housing, as in FIG. 3. The top of the fixation element 18 penetrates body tissue and anchors the lead 10 in the chosen position.

Sometimes the electrical contact or some other property is not as good as desired, and the lead has to be displaced. Then it is easy to rotate the conductor 20 in the opposite direction, and thereby the fixation element 18 is withdrawn from the tissue. In many prior art leads small pieces of the body tissue that are teared off will accompany the fixation element into the electrode assembly 24 and will clog the thread or the like mechanism such that it will jam. In this embodiment, however, such teared off tissue peaces will never reach the guide spring 42, and consequently they will not cause any problem.

Figure 4:
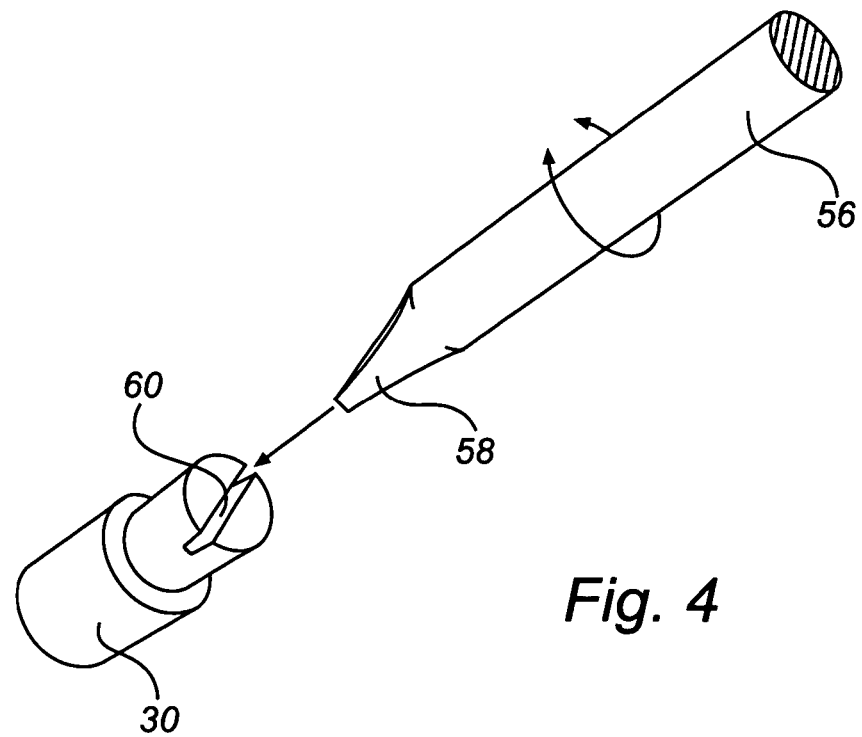
FIG. 4 shows another embodiment of the lead according to this invention, employing a stylet.

In an alternative embodiment the conductor 10 has a centre lumen 54 through which a stylet 56, se FIG. 4, is insertable. At a distal end of the stylet 56 a ridge 58 is formed. The ridge fits into a groove 60 formed in the proximal end 28 of the shaft 30. Thereby, the stylet 56 can be used as a screw driver for screwing out/in the fixation element 18.

Figure 5:
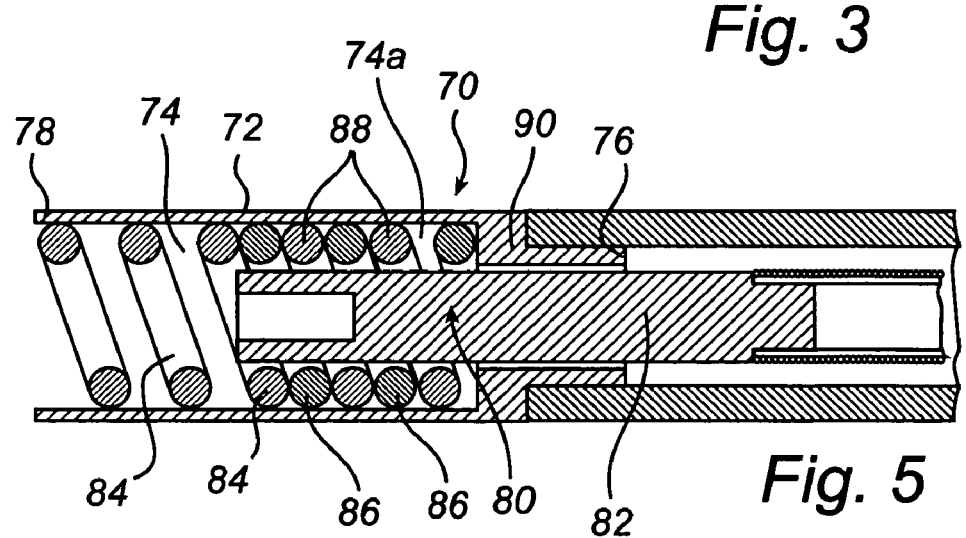
FIG. 5 is a sectional view along a distal end portion of another embodiment of the lead according to this invention.

In another embodiment of the implantable lead, as shown in FIG. 5, the electrode assembly 70 comprises a housing 72, which defines an internal longitudinal cavity 74 and which has a proximal end 76 and a distal end 78. Further, the electrode assembly comprises a fixation assembly 80, which includes a shaft 82, and a helical fixation element 84. The shaft 82 extends into the cavity 74 from the proximal end 76 of the housing 72. The fixation element 84 is attached to the shaft at a distal end thereof and protrudes distally thereof. The fixation assembly 80 is rotatable relative to the housing 72.

The electrode assembly 70 further comprises a helical guide spring 86, which is arranged in a proximal portion 74a of the cavity 74. The guide spring 86 has several turns, which are spaced from each other. The fixation assembly 80 has an interaction portion 88, which interacts with the guide spring 86 for causing longitudinal movement of the fixation assembly 80 when the shaft 82 is being rotated. In this embodiment the interaction portion 88 is a portion of the fixation element 84. More particularly, at least some turns 88 of the fixation element 84 are interleaved with turns of the guide spring 86. The pitches and diameters of the fixation element 84 and the guide spring 86 are the same, and so is the space between the turns. Thus, the turns of the fixation element 84 are fitted into the spaces between the turns of the guide spring such that, in a longitudinal direction of the cavity 74, the turns 88 of the fixation element 84 alternate with the turns of the guide spring 86. When the fixation element 84 is extended by rotating the shaft 74, the turns 88 of the fixation element 84 slides against the adjacent turns of the guide spring 86. In order for the guide spring 86 to be able to feed the fixation element 84 far enough out of the cavity 74, the guide spring has to be long enough and the number of turns in the interaction portion have to be many enough.

The shaft 82 is supported by a single bearing 90, which is arranged at the proximal end 76 of the cavity 74.

Above, embodiments of the implantable lead according to the present invention have been described. These should be seen as non-limiting examples. As understood by a skilled person, many modifications and alternative embodiments are possible within the scope of the invention.

It is to be noted, that for the purposes of this application, and in particular with regard to the appended claims, the word "comprising" does not exclude other elements or steps, that the word "a" or "an", does not exclude a plurality, which per se will be apparent to a person skilled in the art.

Although modifications and changes may be suggested by those skilled in the art, it is the intention of the inventor to embody within the patent warranted hereon all changes and modifications as reasonably and properly come within the scope of his contribution to the art.

We claim:

1. An implantable lead having a proximal end and a distal end, comprising:
   a conductor having a proximal end and a distal end; and
   an electrode assembly, arranged at the distal end of the lead, and comprising: a housing defining an internal cavity and having a proximal end and a distal end
      a helical guide spring arranged in a proximal portion of the cavity and having several spaced turns; and
      a fixation assembly, which is rotatable relative to the housing, the fixation assembly comprising;
         a shaft, the shaft extending into the cavity from the proximal end of the housing, and
         an extendable helical fixation element attached to the shaft at the distal end thereof and protruding beyond the distal end thereof; wherein the fixation assembly has an interaction portion and
   said guide spring being in mechanical connection with said housing at at least one of said ends of said housing to cause the interaction portion of the fixation assembly to extend into a space between, and slide against, the adjacent turns of the helical guide spring to longitudinally move the fixation assembly, when the shaft is rotated.

2. An implantable lead according to claim 1, wherein the interaction portion comprises a portion of the shaft having a protrusion, which extends into the space between the turns of the helical guide spring.

3. An implantable lead according to claim 2, wherein the electrode assembly further comprises a first bearing for the shaft, wherein the first bearing is attached to the inner wall of the housing, and wherein the first bearing supports the shaft between the distal end of the shaft and the protrusion.

4. An implantable lead according to claim 3, wherein the electrode assembly further comprises a second bearing for the shaft, wherein the second bearing is arranged at a proximal end of the cavity.

5. An implantable lead according to claim 4, wherein the first and second bearings define a chamber of the cavity, which chamber is fillable with a lubricant.

6. An implantable lead according to claim 2, wherein the protrusion is post shaped.

7. An implantable lead according to claim 2, wherein protrusion abutment surfaces of the turns are curved and corresponding spring abutment surfaces of the protrusion are shaped for minimizing the contact area between the protrusion and the turns of the guide spring.

8. An implantable lead according to claim 2, wherein the shaft has several protrusions, which are symmetrically arranged around the shaft.

9. An implantable lead according to claim 1, wherein the interaction portion comprises a portion of the helical fixation element having turns equally spaced as the turns of the guide spring and extending in the space between the turns of the guide spring.

10. An implantable lead according to claim 1, wherein the conductor is mechanically connected with the shaft.

11. An implantable lead according to claim 1, wherein the shaft is arranged to be rotated by rotating the conductor.

12. An implantable lead according to claim 1, wherein the lead has a lumen through which a stylet is insertable, and wherein the shaft is arranged to be rotated by means of the stylet.

13. An implantable lead according to claim 1, wherein the helical fixation member and the helical guide spring have the same pitch and are interleaved with one another.

14. An implantable lead according to claim 1, wherein the shaft has several protrusions, which are symmetrically arranged around the shaft and fit into the turns of the helical guide spring.

15. An implantable lead according to claim 1, wherein the helical fixation element has turns that are interleaved with, and slide against, the turns of the helical guide spring to thereby cause longitudinal movement of the helical fixation element relative to the helical guide spring when the shaft is rotated.

16. An implantable lead according to claim 1, wherein the interaction portion causes the shaft and fixation assembly to longitudinally move relative to the helical guide spring as the shaft rotates and the interaction portions slide against the turns of the helical guide spring.

\* \* \* \* \*